US006733448B2

(12) United States Patent
Kelly et al.

(10) Patent No.: US 6,733,448 B2
(45) Date of Patent: May 11, 2004

(54) METHOD OF TRANSMITTING ULTRASONIC SCAN DATA

(75) Inventors: Kevin M. Kelly, Venice, CA (US); Roger Royce, Venice, CA (US); Matthew Warren Smith, Tulsa, OK (US)

(73) Assignee: Sonocine, Inc., Venice, CA (US)

( * ) Notice: Subject to any disclaimer, the term of this patent is extended or adjusted under 35 U.S.C. 154(b) by 0 days.

(21) Appl. No.: 10/328,227

(22) Filed: Dec. 23, 2002

(65) Prior Publication Data

US 2003/0125626 A1 Jul. 3, 2003

Related U.S. Application Data

(62) Division of application No. 09/687,128, filed on Oct. 13, 2000, now Pat. No. 6,524,246.

(51) Int. Cl.[7] .................................................. A61B 8/00
(52) U.S. Cl. ...................................................... 600/437
(58) Field of Search .............................. 600/437–472; 73/620–633; 367/7, 11, 130, 138; 128/916

(56) References Cited

U.S. PATENT DOCUMENTS

| 4,094,306 A | 6/1978 | Kossoff ...................... 128/2 V |
| 4,167,180 A | 9/1979 | Kossoff ...................... 128/660 |
| 4,347,850 A | 9/1982 | Kelly-Fry et al. ........... 128/660 |
| 4,489,729 A | 12/1984 | Sorenson et al. ............ 128/660 |
| 4,905,700 A | 3/1990 | Wokalek et al. ........ 128/660.01 |
| 5,152,290 A | 10/1992 | Freeland ................. 128/660.07 |
| 5,318,028 A | 6/1994 | Mitchell et al. ........ 128/660.08 |
| 5,329,929 A | 7/1994 | Sato et al. .................... 128/660 |
| 5,333,612 A | 8/1994 | Wild ........................ 128/660.9 |
| 5,433,202 A | 7/1995 | Mitchell et al. ........ 128/660.08 |
| 5,454,371 A | 10/1995 | Fenster et al. ......... 128/660.07 |
| 5,474,072 A | 12/1995 | Shmulewitz ........... 128/660.09 |
| 5,479,927 A | 1/1996 | Shmulewitz ........... 128/660.09 |
| 5,524,636 A | 6/1996 | Sarvazyan et al. ........... 128/774 |
| 5,562,095 A | 10/1996 | Downey et al. ........ 128/660.09 |
| 5,640,956 A | 6/1997 | Getzinger et al. ........ 128/653.1 |
| 5,664,573 A | 9/1997 | Shmulewitz ........... 128/660.09 |
| 5,770,801 A | 6/1998 | Wang et al. ................... 73/644 |
| 5,833,634 A | 11/1998 | Laird et al. .................. 600/587 |
| 5,842,473 A | 12/1998 | Fenster et al. ......... 128/660.09 |
| 5,860,934 A | 1/1999 | Sarvazyan .................... 600/587 |
| 5,938,613 A | 8/1999 | Shmulewitz ................. 600/461 |
| 5,984,870 A | 11/1999 | Giger et al. ................ 600/443 |
| 5,989,199 A | 11/1999 | Cundari et al. ............. 600/587 |
| 6,002,958 A | 12/1999 | Godik ......................... 600/407 |
| 6,027,457 A | 2/2000 | Shmulewitz et al. ....... 600/562 |
| 6,117,080 A | 9/2000 | Schwartz .................... 600/443 |
| 6,119,033 A | 9/2000 | Spigelman et al. ......... 427/429 |

FOREIGN PATENT DOCUMENTS

| EP | 0452532 A1 | 10/1991 |
| EP | 0 882 426 A | 12/1998 |
| JP | 04 183453 A | 6/1992 |
| WO | 98 47428 A | 10/1998 |
| WO | 00/51484 | 9/2000 |

*Primary Examiner*—Ali M. Imam
(74) *Attorney, Agent, or Firm*—Fulbright & Jaworski L.L.P.

(57) ABSTRACT

A method of transmitting scan data from an ultrasonic scanning device to a computer. A desired number of individual scan images are acquired as frames within a buffer, after which the contents of the buffer are frozen. The number of frames in the frozen buffer are counted, and the dimensions and pixel format of each frame in the frozen buffer are determined. The frames from the scanning device are transmitted to the computer via a connection device, and the transmitted frames are written to an image file in a sequential manner.

7 Claims, 10 Drawing Sheets

SCHEMATIC DIAGRAM SHOWING A PLURALITY OF SCAN ROWS OF SCREENING
IMAGES MADE IN A RIGHT LATERAL SCAN OF A HUMAN BREAST

SCHEMATIC OF A PREFERRED EMBODIMENT OF A FILE THAT INCLUDES A
PLURALITY OF SCAN ROW IMAGES

FILE CREATION
USER INTERFACE

PLAYBACK USER INTERFACE

POSITION CALCULATOR
IN VIEWING PROGRAM

METHOD OF TRANSMITTING ULTRASONIC SCAN DATA

This is a divisional application of U.S. patent application Ser. No. 09/687,128, filed Oct. 13, 2000 now U.S. Pat. No. 6,524,246 in the name of Kevin M. Kelly et al., for which priority under 35 U.S.C. 120 is claimed. The disclosure of U.S. patent application Ser. No. 09/687,128 is incorporated herein by reference.

FIELD OF THE INVENTION

The field of the present invention is ultrasonic scanning and diagnostics for cellular tissue.

BACKGROUND OF THE INVENTION

Ultrasonic probes have been used for scanning cellular tissue for many years. Presently, any medical ultrasound examination, whether of the heart, pelvis,; abdomen, soft tissues or any other system, is usually displayed as a number of individual frames or pictures from a study performed in a dynamic movie-like manner. The usefulness of the scan, however, is dependent on the skill of the operator, who manipulates the probe by hand while watching the scan images on a monitor to identify areas of interest. Once these areas are identified, the operator usually records single or multiple single scan images showing those areas.

Because the operator must choose a few frames from the large number generated during the scan, the process is open to error. The operator may fail to select an image of an important finding, or may select an image that misrepresents the overall findings. In addition, since the operator is manipulating the probe by hand, and the speed of the probe over the tissue cannot be correlated with the image capture rate of the probe, the coverage of the scanned tissue is somewhat haphazard. As a result, the operator does not record a series of images that represent a contiguous and complete set of images for the entire scanned tissue. Nor does the manual operation of the probe allow for entirely uniform coverage of the tissue, even if multiple passes are used.

A second method of recording ultrasonic examinations is used for dynamic examinations such as echocardiography, where a dynamic recording is made on videotape. Unfortunately, this analog method is not matched to the digital sonographic recording of individual frames. Consequently, there is a great loss of detail that prevents the evaluation of individual frames, which limits the usefulness of the videotape for diagnosing tissue anomalies. In addition, the use of separate videotapes for individual patients is expensive, and creates a storage problem because of the bulkiness of the tapes. The interpreting physician has no way to vary the speed of playback or to vary the size of the images. Nor can the physician vary the inherent contrast and brightness of the images, only the monitor settings. These difficulties lengthen the review time and prevent optimum viewing.

Specific to screening asymptomatic women for occult breast cancer, there are two methods presently in widespread use, physical examination and mammography. Both of these methods are imperfect. Physical examination, whether performed by the woman herself or by a physician or other health care provider, usually cannot detect cancers smaller than ½ inch in diameter. Some cancers have to be many times larger to be detected. Mammography is unable to detect as many as 30 percent of cancers smaller than ½ inch. About 5 to 10 percent of larger cancers are mammographically occult. Mammograms also use radiation and necessitate painful compression of the breasts, which discourage women from having routine mammograms.

Although not well recognized by the medical community, ultrasound is very proficient at diagnosing breast cancers if the location of the abnormality is first discovered by another modality, such as mammography or physical examination. When using ultrasound as a screening method for the entire breast, however, malignancies are usually difficult to pick out of the background tissue. In the past there have been two schemes to use ultrasound for breast screening, but they failed to gain acceptance due to their unacceptably low success rate in finding cancers.

One method was a water bath system with multiple ultrasound probes and the breast in a water bath that allowed generation of images of the whole breast in consecutive slices. These slices could be viewed in sequence at a rate of one every ten seconds.

The second method was to videotape-record the scanning performed by a technician examining the entire breast. This method had the disadvantage of being somewhat haphazard in breast coverage. The variable speed of manual motion does not allow the tissue to be uniformly imaged because the speed is not synchronized to the frame capture rate of the ultrasound probe. Videotaping also results in a degradation of the images for the reasons described above.

To date, no method has been developed to uniformly and reliably use ultrasound probes to create a contiguous and complete set of scan images for an entire area of cellular tissue, such as a human breast. Ultrasound is usually used to investigate areas of interest in cellular tissue that have already been identified by other screening methods such as mammograms, x-rays, and MRI-scans. Ultrasound is not ordinarily used as a screening tool for cellular tissue anomalies.

SUMMARY OF THE INVENTION

The present invention is directed to an improved system of ultrasonic scanning and diagnostics of cellular tissue. A sequence of cross-sectional ultrasonic images of tissue are generated, with means to determine the location of each individual image. A method of transmitting the scan data from an ultrasonic scanning device to a computer includes acquiring a number of individual scan images within the buffer of the scanning device. The buffer is frozen upon acquisition and the number of frames are counted and the dimensions in pixel format of each is determined. The results are then transmitted to a computer and converted to a format used by a viewer program. The converted frames are then written to an image file in a sequential manner.

Accordingly, it is an object of the present invention to provide a system and method that will allow cellular tissue to be reliably screened for anomalies by ultrasonic scanning. Other and further objects and advantages will appear hereafter.

DETAILED DESCRIPTION OF A PREFERRED EMBODIMENT

Figure 1:
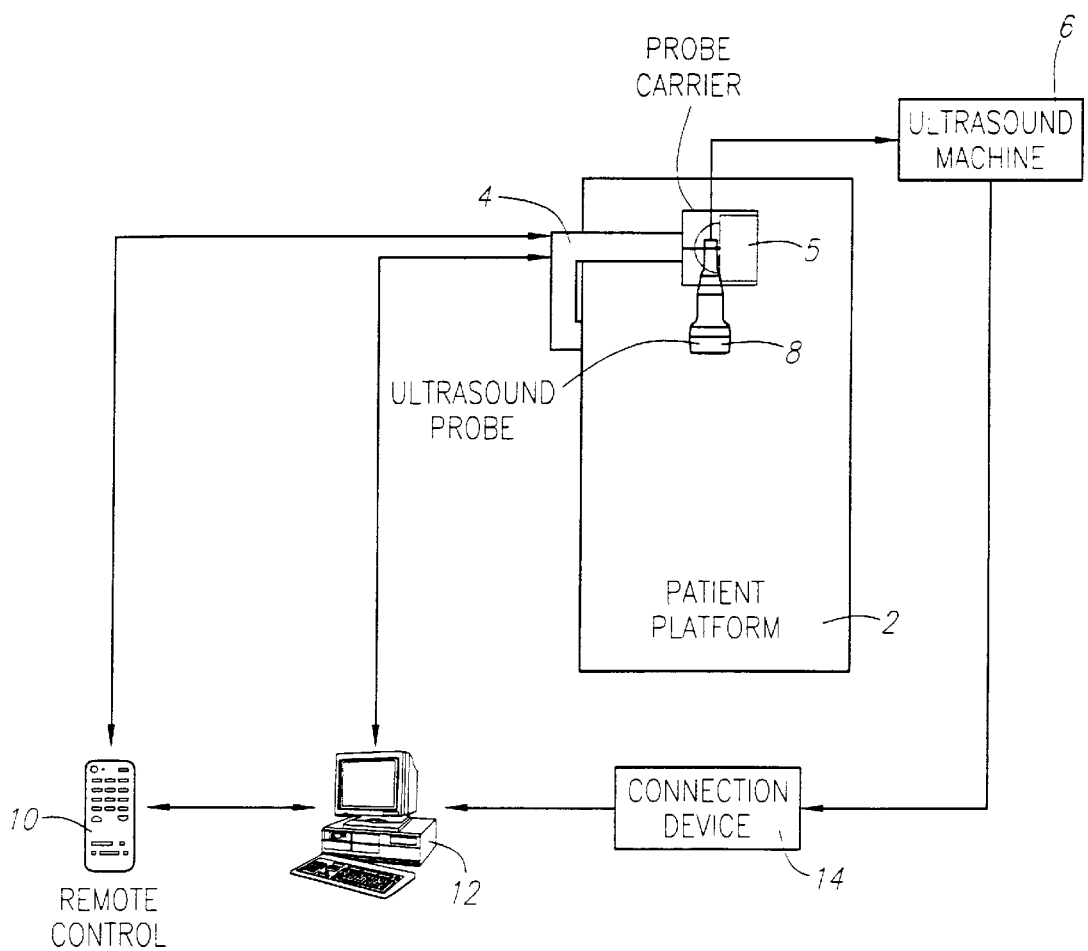
FIG. 1 is a block diagram showing the elements of a cellular tissue screening tool and its interconnections.

As shown in FIG. 1, a preferred embodiment is comprised of a patient platform 2 to steady the patient and provide a base for the support member 4, the probe carrier 5 connected with the support member 4 that is capable of translational movement to guide the probe across the tissue to be scanned, a standard medical ultrasound device 6 with an associated probe 8, a remote control device 10 that operates the probe carrier 4, a standard computer 12, a connection device 14 between the ultrasound device 6 and the computer 12, and a viewing program that obtains images from the ultrasound device and converts them into images compatible with the viewing program and displays the images. The medical ultrasound scanning device 6 with associated probe 8, computer 12, and connection device 14 are commercially available.

The mechanical carrier 4 holding the ultrasound probe 8 can be connected with the ultrasound scanner 6. Synchronization between the probe holder mechanical carrier 4 and the ultrasound scanner 6 can be employed while recording the scans.

Probe Carrier

Figure 2:
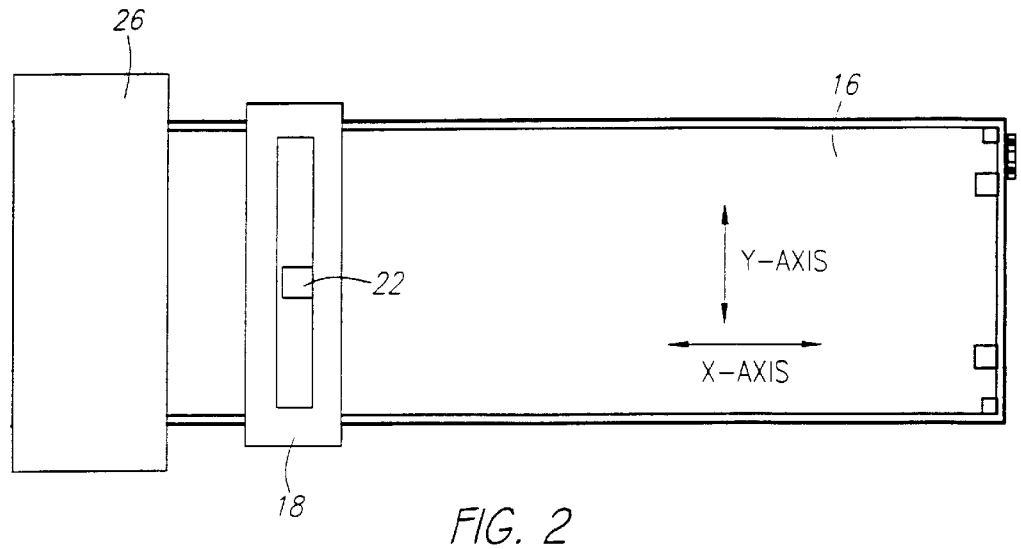
FIG. 2 depicts a plan view of a patient platform and probe carrier.
Figure 3:
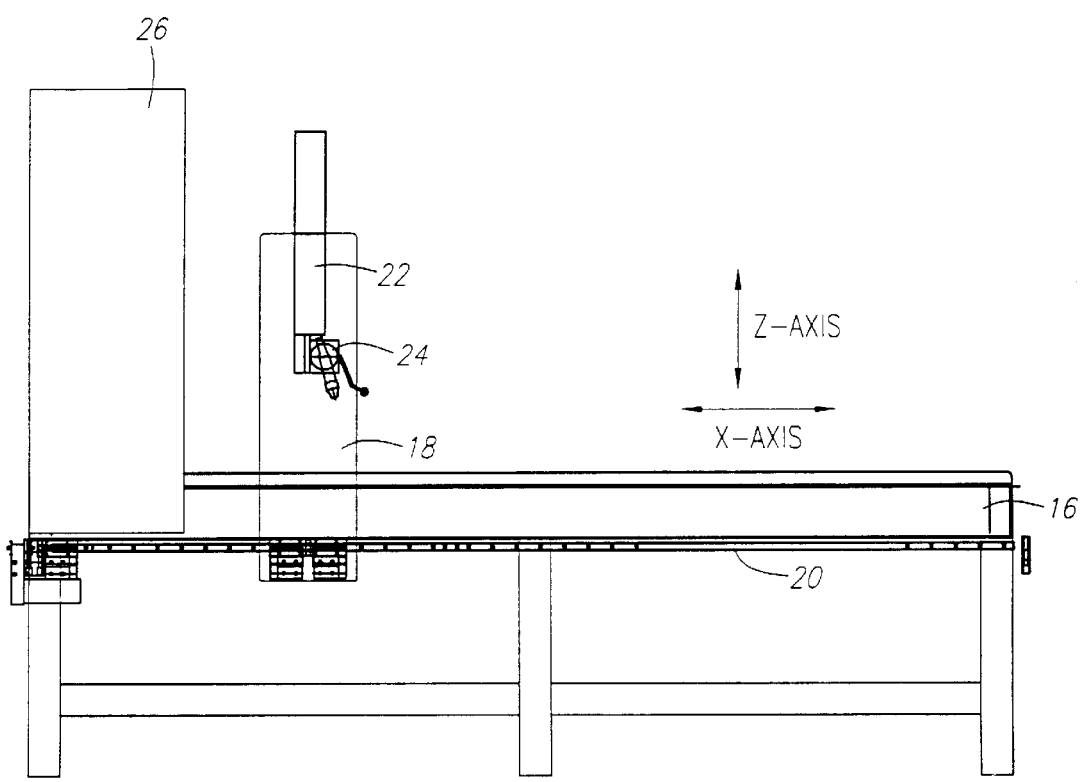
FIG. 3 depicts a side view of a patient platform and probe carrier.
Figure 4A:
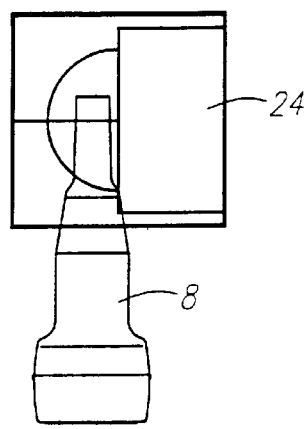
FIG. 4A depicts a portion of a probe carrier holding an ultrasonic probe.
Figure 4:
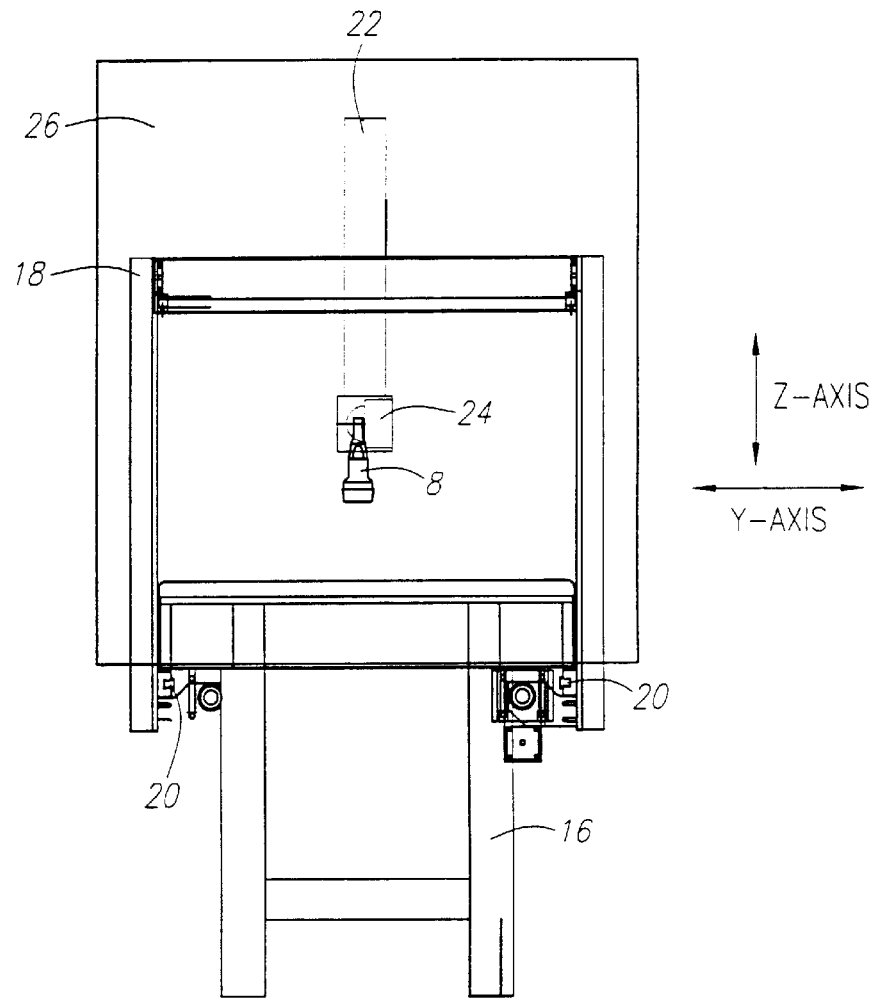
FIG. 4 depicts an end view of a patient platform, and the probe carrier holding an ultrasonic probe.

In order to obtain substantially parallel and contiguous images, a mechanical device holding the ultrasound probe 8 propels the probe across the tissue to be scanned at a uniform rate. In a preferred embodiment shown in FIG. 3, the probe carrier is mounted to a patient platform 16 that steadies the patient during the exam and acts as a base for the mechanical probe carrier. The carrier carriage 18 shown in FIGS. 2 and 3 is comprised of two parallel vertical members attached to rails 20 beneath the platform and a horizontal member that is attached to the top of the two vertical members, as shown in FIG. 4. The rails 20 allow the carriage 18 to move along the length of the platform, or the x-axis, as shown in FIGS. 2 and 3. Attached to the horizontal member between the two vertical members is another vertical member, called the carrier arm 22, with the carrier 24 holding an ultrasound probe 8 at its lower end. The carrier arm 22 is attached in such a manner that allows it to move along both the y-axis and the z-axis, so that it can move both across the patient and nearer/further from the patient on the platform, as shown in FIG. 4. The carrier 24 itself is articulated to hold the probe at any desired angle relative to the patient by rotating about the x and y axes. The carrier 24 holds the probe 8 at a fixed angle during scanning. In another embodiment, the carrier 24 dynamically angles the probe 8 during the scanning process to keep it perpendicular to the patient's skin (or any other preferred orientation).

To protect the carriage assembly when not in use, and to prevent the patient from becoming entangled in it when first lying on the platform, the assembly is housed in a "garage" 26 at one end of the platform 16. In a preferred embodiment, the carriage 18 is propelled along the x-axis of the platform 16 during scanning by one or more motors that are controlled by a microprocessor. The carrier arm 22 is also moved along its two axes during scanning by one or more motors controlled by one or more microprocessors. The microprocessor(s) can be separate from the computer that operates the viewing program (described below), or the computer can be used for this purpose. The carrier arm 22 moves along the z-axis to maintain consistent contact between the probe 8 and the patient's skin during scanning. The carrier arm 22 maintains a constant pressure of the probe 8 on the patient, with a user-selected preset value. This pressure is monitored during the scan and an override function will move the carrier arm 22 up and away from the patient in the z-axis if a maximum pressure level is detected. In another embodiment, the operator will maintain the pressure manually during the scanning process, and the pressure may be measured using pressure transducer(s) in close proximity to the probe head. The carrier arm 22 will move upward to clear the patient at the end of the scan. A manual override on the remote control 10 is also available to move the carrier arm 22 away from the patient when there is a panic or emergency situation.

In other embodiments, the carriage and carrier arm can be either on a parallel track arrangement (one sided or multi-sided), or be comprised of an articulating arm or some other contrivance, located over, underneath or adjacent to the patient (with or without the use of a patient platform) positioned either upright or prone. The carrier arm need not be supported by a carriage assembly connected to the patient platform, but could be independently suspended from the ceiling, wall, or floor. The carrier mechanism could be similar to carriage mechanisms currently used to support x-ray machines, with means added to provide the requisite movement of the probe. The probe may be supported and propelled by the mechanical carrier by any means (manually, mechanically, electrically, hydraulically, pneumatically or by any other means, with or without control feedback), or any combination of methods. These methods, singularly or combined may be utilized to control the probe in the X, Y and Z-axes. Gravity may also be employed to provide the requisite pressure of the probe on the patient, or assist in the propulsion of the probe across the tissue.

The probe may be designed as a permanent or removable component of the mechanical carrier. The carrier may be designed with or without an onboard integrated ultrasound machine, ultrasound probe, and or ultrasound probe interface.

The carrier 24 can be articulated to change the angular position of the probe 8 prior to or during scanning either manually, or by one or more motors controlled by one or more microprocessors. The microprocessor(s) can be separate from the computer that operates the viewing program (described below), or the computer can be used for this purpose. The pitch axis tilts the probe 8 forward and backward, rotating it about the y-axis, and the roll axis tilts the probe 8 left and right, rotating it about the x-axis. The pitch and roll axes maintain full contact between the probe and the skin surface by maintaining the probe 8 at a perpendicular angle to the skin, to allow for optimal ultrasonic imaging.

In an embodiment where the probe's angular position is adjusted automatically during scanning, the pitch and roll adjustments are triggered by one or more displacement transducers positioned around the ultrasound probe 8. In this embodiment, all the data related to the position and angle of the probe 8 are provided to the viewing program to allow the images to be correlated with their corresponding location on the patient. The position data allow the program to compensate for the overlapping of, or gaps between images. The measurement system can be by any means or convention and may consist of any or all of X, Y, Z-axes and/or the probe angular position.

The speed of the carrier 24 holding the probe 8 is precisely controlled by a microprocessor, and the speed is correlated with the capture rate of the ultrasonic scanning device 6. The uniform speed of the carrier 24 results in images that are uniformly spaced, which allows the viewing program (discussed below) to calculate the position of a selected point on any image. In an embodiment where the probe is held at a fixed angle during the scan, the uniform spacing is all that is necessary to determine the position of each frame of the scan on the patient. The ultrasound scanning device 6 acts as a controller in communication with the probe 8 to sequentially activate the probe 8 as it moves across the tissue, but any other controller could be used to activate the probe, including a computer linked to the probe or the scanning device or both.

When used for breast tissue scanning, the operator will determine the amount of area of the breast for scanning. In current practice, the width of the tissue scanned by the ultrasound probe is generally too small to capture an image of an entire organ, such as the breast. As a result, several adjacent passes are performed to provide complete coverage. Each pass (called a scan row) will have some overlap with the preceding pass, to achieve full coverage and eliminate the potential for missing features at the fringes of the scan. Prior to each successive pass, the carrier arm 22 lifts away from the patient, moves along the y-axis across the breast and along the x-axis to the top of the breast to position itself for the next scan row, then lowers itself along the z-axis onto the patient.

Figure 5:
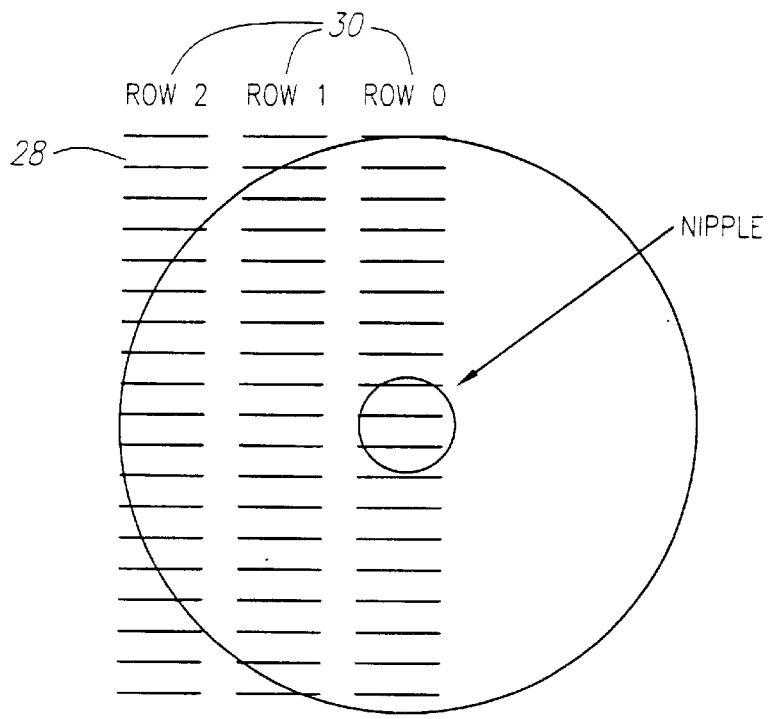
FIG. 5 is a schematic diagram showing a plurality of scan rows of scan row images made of a right lateral scan of a human breast.

A scan row contains a plurality of individual images or frames, typically about 200 to 300 for a breast. FIG. 5 depicts how the frames 28 in scan rows 30 are aligned on a typical breast scan, but for clarity, no overlap is shown. A scan row 30 can be thought of as a stack of photographic slides, each slide representing an individual frame 28. The frames 28 are evenly spaced. This may be accomplished by uniform motion of the probe 8 and uniform timing of the scans. The frames are most conveniently substantially parallel to each other.

In another embodiment, the probe's 8 angular position is dynamically adjusted during scanning to follow the contours of the tissue being scanned. In that embodiment, the tops of the frames are evenly spaced, and the tissue contours will be sufficiently gentle that adjacent frames will remain substantially parallel to each other, although they may differ by as much as a few degrees. Although adjacent frames within a single scan row are substantially parallel, frames may become progressively less parallel as they are separated by an increasing number of frames. Frames in two adjacent scan rows are not necessarily substantially parallel.

In a preferred embodiment, two breasts are scanned in four segments, each segment consisting of one-half of a breast. Each segment consists of multiple scan rows 30, with the first scan row aligned at the center of the breast over the nipple and successive scan rows being progressively further from the nipple. FIG. 5 depicts a series of scan rows 30 that make up one segment. In other embodiments, each breast may be scanned in one or more segments, with the scan rows progressing across the entire breast from lateral to medial, or vice-versa.

Viewing Program

The viewing program preferably has the following overall features:

a) It allows the entry and storage of demographic and other written data about each patient.

b) It extracts multiple series of the scanning data from the ultrasound scanning device either as a single image, a completed data set from a cine loop or as real-time continuous data from video streaming.

c) It assembles this data into a single or a number of individual frames for viewing.

d) It may present the multiple data series as descriptive titles on a content page for subsequent review by the operator.

e) In the case above, when each descriptive title is selected, the corresponding data series is loaded and displayed by the viewer.

f) It is able to present the frames from each data set as individual images that are displayed on a monitor at a variable rate. This rate can be sufficiently fast to impart a movie or cine-like quality to the images. The frames can be also displayed at a slow rate or even as still pictures for more intense study.

g) It is able to display the images at variable magnification and with a variety of imaging enhancements that make anomalies more pronounced and visible, including variable contrast and brightness, gamma correction, etc.

h) It acts as a recorder, able to store the information from each patient scan on a data storage device such as a computer hard disk and on any temporary or permanent data storage device such as compact disks (CD's).

i) Along with the patient scan data, it may incorporate a stand-alone viewer program on each CD or other storage media.

j) It allows the transfer of single or multiple images to the Internet, printers or other image programs, such as PowerPoint or PhotoShop.

k) It allows for the translation of the scan data into the DICOM format for use by other proprietary software.

l) During image review, it emits an audible signal, a visual signal, or both, that identifies the end of each scan row, segment, and breast, to identify the relative position within the scan data without requiring the user to look away from the images in order to assess the relative position within the image sequence.

A preferred embodiment of the viewing program (or viewer) is a streamlined, monolithic, 32-bit Windows application designed to run on Windows 95, Windows 98, NT 4, and Windows 2000. A preferred embodiment is implemented to interface with and acquire data from the General Electric Logiq 700 medical ultrasound scanner. The viewing program could, of course, be written to run on other types of computer systems and future versions of operating systems, and to interface with other types of scanning devices. As used in the claims, "computer" generically refers to any suitable device using one or more microprocessors to process data.

The viewing program's monolithic structure and relatively small size allow it to be bundled with the image data for ease of transport and viewing flexibility. In most cases, complete scan data for a patient and the program can be placed on a single CD, allowing the user to transport a number of patient scans in a relatively small package, and view them on any computer that is compatible with the software on the CD., Although it would be even more convenient to transmit scans via e-mail, the current speed and size limitations of e-mail make sending the entire scan impractical. If desired, however, the viewing program can select small segments of the scan data and bundle it with the viewing program, for a small data package that is practical to send via current e-mail systems. Other delivery options could also be utilized, such as streaming video over the internet, or discrete file downloads using file compression to speed download time. To satisfy medical regulatory requirements, a lossless compression technique should be used, such as Portable Network Graphics (PNG), or other lossless schemes.

In other embodiments, the viewing program could be designed to operate solely on a computer on which it resides, or it could be resident on a server in a client-server environment. The program could also be non-monolithic, using Java or a similar language, in a network-centric environment. Given the rate at which software programming and computing hardware are developing, there are limitless variations of how to implement the software and hardware to achieve the desired result of the viewing program.

In a preferred embodiment shown in FIG. 1, the viewer program controls the scanning operation and data offloading via a connection device 14, such as a network TCP/IP interface. Other connection devices could be used, or with certain scanners, none may be needed. The General Electric Logiq 700 ultrasonic scanning device has an internal buffer that can store a finite amount of image data before offloading is required to clear the buffer for another scan. Other scanning devices have no such buffer, but instead provide an output of streaming data as the scan is being performed. Although a preferred embodiment uses a scanning device with a buffer, the program is capable of acquiring image data from scanning devices that continuously offload streaming data. Other embodiments with different data outputs from the scanning device can also be used with the viewing program.

Figure 6:
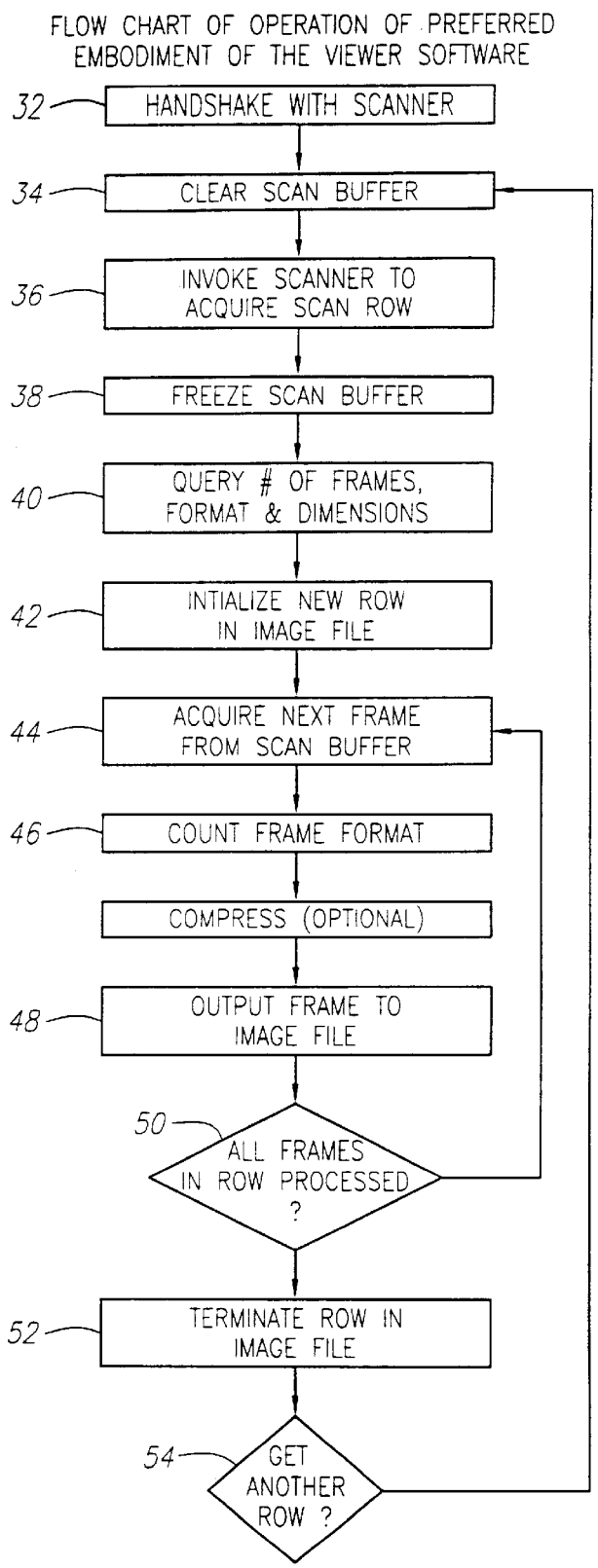
FIG. 6 is a flow chart describing how the viewing program on the computer acquires data from the ultrasonic scanner, converts it into digital image data that can be used by the viewing program, and creates an image file.

In a preferred embodiment, the computer acts as a receiver and recorder for the ultrasonic images obtained from the ultrasonic scanning device. As shown in FIG. 6, a preferred embodiment uses a handshake sequence between the viewer and scanner to begin the scan acquisition process 32. The viewer then invokes the scanner to clear its internal frame buffer 34 and then to acquire a scan row to its internal buffer 36. The viewer freezes the scanner buffer 38, determines the number of frames in the buffer, their dimensions and pixel format 40, initializes a new scan row in the image file 42, reads individual frames from the buffer 44, counts the frame format 46 and writes them into the image file 48 on a data storage device. It then repeats the acquisition process until all the frames in the scan row are processed 50, and terminates the scan row in the file 52. It then starts all over with additional scan rows until the entire scan is acquired in the image file 54. A preferred embodiment of the viewer uses a proprietary image file format, which contains a header for patient information and scan information ("image file"). In another embodiment, the viewing program converts the image data into a DICOM format, which also contains a header for patient information and scan information. DICOM stands for "Digital Imaging and Communications in Medicine," and is a standard developed by ACR-NEMA (American College of Radiology—National Electrical Manufacturer's Association) for communications between medical imaging devices.

Figure 7:
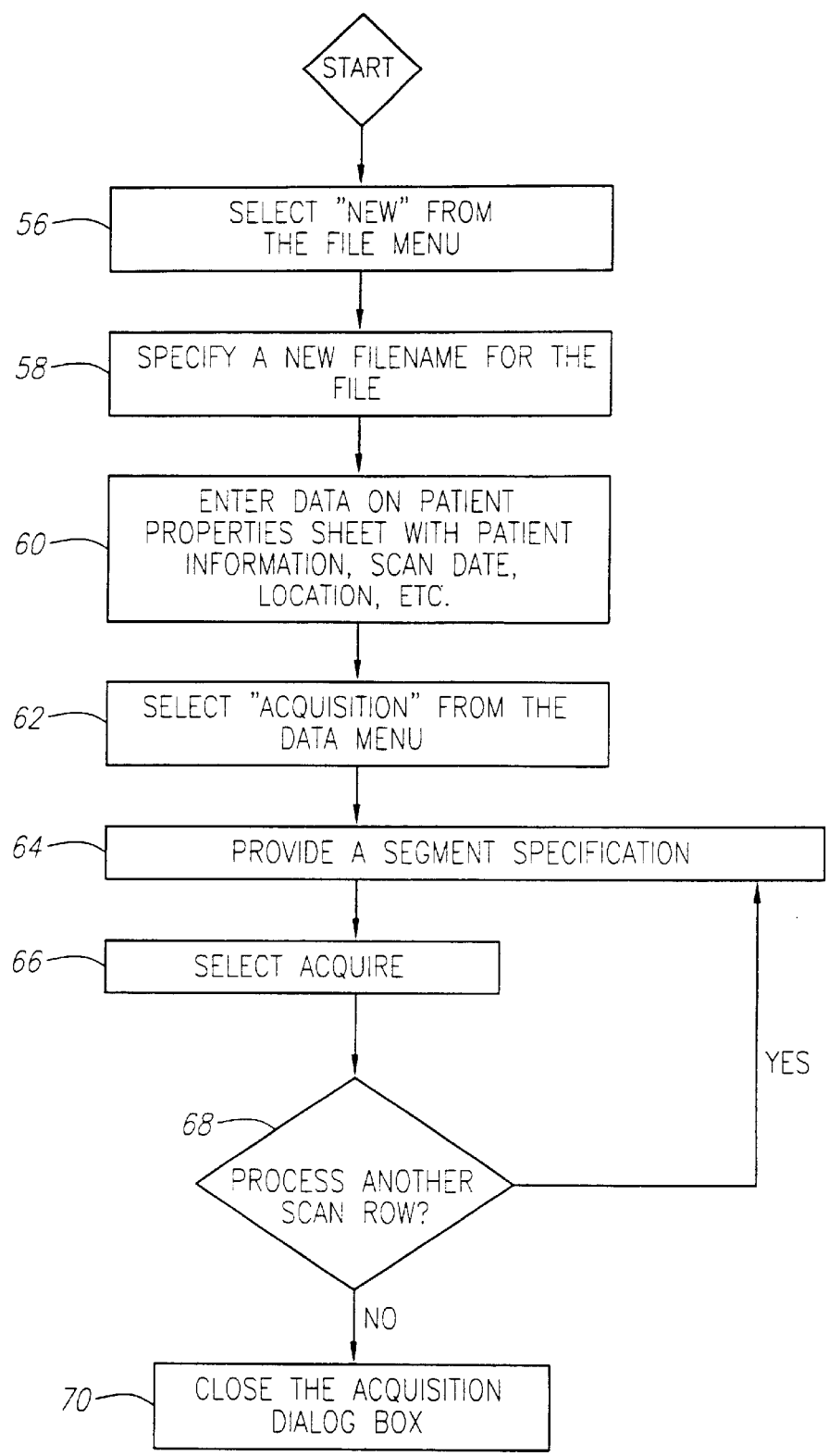
FIG. 7 is a flow chart describing how a user interface of the viewing program operates to acquire data from the ultrasonic scanner and create an image file on the computer.

FIG. 7 is a flow chart showing the user interface for the data transfer process from the scanner to the computer. The user creates a new file by choosing from the file menu 56, specifies a name for the new file 58, enters the patient data and relevant information 60, makes a selection from the data menu 62, and specifies what segment of the breast is about to be acquired 64. The user then begins the acquisition process 66, and frames are then offloaded sequentially from the scanner's frame buffer via a connection device 14, such as a network interface, then normalized, compressed losslessly (if desired) and written sequentially to the image file, said file recorded on a data storage device. When all buffered frames are processed, the viewer terminates the constructed row in the image file 68. Another scan row can then be acquired and so on, or the interface to the scanner may be terminated 70.

For offloading streaming data, the program performs a real-time write-through. The program queries the scanner for the image format before beginning the acquisition. Then it buffers a single frame at a time and writes that one frame to a data storage device, before obtaining another frame through the sockets interface.

Acquiring The Data

Figure 8:
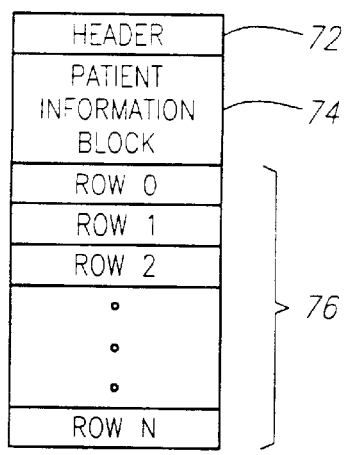
FIG. 8 is a schematic of a preferred embodiment of an image file containing a plurality of scan row images.

In a preferred embodiment, the viewer creates (and subsequently displays) proprietary image files, the format of which consists of a file header 72, a patient information block 74, and zero or more blocks of scan row frames 76, as shown in FIG. 8. The patient information block 74 contains not only information about the patient, but also information about the scan itself, such as the depth and width of the scan, length of the scan row, speed of the carrier during the scan, the number of frames per second captured by the scanner, the spacing between each frame, etc.

In another embodiment where the probe's angular position is dynamically adjusted during the scan, the viewer program records on a data storage device the angular position of each frame and other information for each frame. The angular position data can be provided to the viewer program though the scanner 6, from sensors attached to the probe 8 or the carrier 5, or from an intermediary computer program that gathers this data.

Rows appear in the image file in the order they are acquired, not necessarily the order in which they will ultimately be displayed by the viewer. Any number of scan rows may be included in an image file and there is no limit to the size of an image file. The data in an image file are laid out in such a manner that frames within a row are advanced in the order in which they will be displayed. This enables the viewer to do efficient read-ahead buffering during display for optimal viewing smoothness.

The viewer is implemented to be largely independent of the particular scanner hardware with which it is paired. A specific module written for each scanner is responsible for "normalizing" data from the internal format used by that particular scanner to the format used within an image file. Scan row frame elements stored in an image file are written in a format optimized for rapid rendering during display. In a preferred embodiment, the viewer is run on computers using a WIN 32 operating system, and scan frames are written to image files in an 8-bit format that closely mirrors 8-bit grayscale Windows DIB (device-independent bitmap) format. This allows the images to be efficiently displayed on a Windows computer with practically no routine translation.

A preferred embodiment pairs the viewer program with the General Electric Logiq 700 ultrasound scanner. To translate frame data from the format used internally by the Logiq 700 or any other scanner, each specific normalizing filter performs several operations to the format used by the viewer when creating image files. In the Logiq 700, these operations include the following:

1. Byte #3 (the fourth byte) of every D-word is stripped
2. Transparent color value 255 is normalized to 0
3. Scan lines are inverted
4. Byte ordering is changed from "Big Endian" to "Little Endian"
5. Scan lines are aligned to 4-byte boundaries When interfacing with a different scanner device, different normalization operations would be appropriate.

Displaying the Images

After acquiring, converting, and storing the scan data, the second major task of the viewer is to display the scan images. The viewer opens a previously created image file and renders sequential scan row frames within its interface in a "movie-like" manner. In a preferred embodiment for breast cancer screening, a breast can be divided into two parts; from the nipple toward the axilla is the lateral half, and from the nipple toward the sternum is the medial half. A set of scan rows for each breast half is called a "segment," and thus there are four segments for two complete breast scans. The viewer arranges all scan rows such that they are displayed beginning with right lateral scan rows (arranged such that subsequent right lateral rows are progressively more lateral), and then proceeding to right medial scan rows (arranged such that subsequent rows are progressively more medial). The viewer then proceeds to left medial scan rows, and then to left lateral scan rows. Although the above arrangement of the scan rows is implemented in a preferred embodiment, different arrangements could be used in other embodiments.

Figure 9:
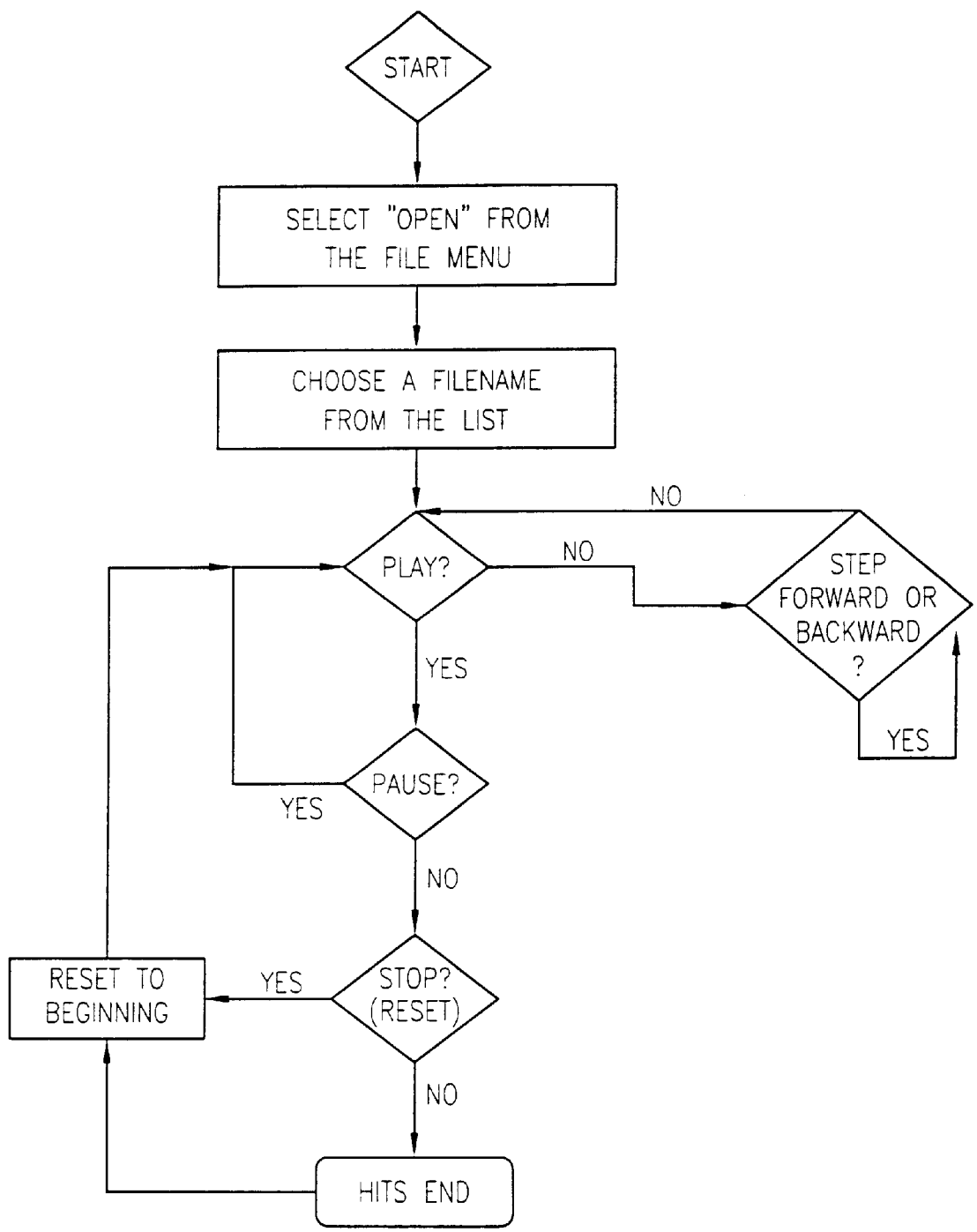
FIG. 9 is a flow chart describing how the user interface of the viewing program operates during playback of images on the computer.

The viewer's user interface provides access to these features and capabilities:

1. Play, pause, and reset scan row playback
2. Step forward and backward between sequential frames
3. Adjust playback frame rate
4. Jump forward and backward between scan rows
5. Export single frames and sets of frames as standard bit-mapped images
6. Select a start point and end point in the frame sequence and loop playback over that selected frame scan
7. Adjust the brightness and contrast of displayed frames
8. Apply imaging enhancements to make features or anomalies more visible
9. Print single frames and sets of frames
10. Measure features displayed on certain frames, given the physical height and width of the frames
11. Calculate the physical location of a point of interest (POI) on a particular frame given a reference point (RP) (on the same frame or a different frame), the physical dimensions of the frames, the Z-coordinate spacing between frames and the X-coordinate overlap of frames on subsequent scan rows
12. Alter the frame magnification The user interface for the viewing program looks and operates in largely the same manner as commercially available digital video players, such as Microsoft Windows Media Player, with buttons for Play, Pause, Stop, a slider bar to move back and forth within segments, etc. The playback features utilize standard Windows input/output operations commonly used in digital video applications. A generalized flow diagram showing the user interface steps for playback operation is shown in FIG. 9.

One of the viewer features is the ability to determine the physical location (on the patient) of any point on any frame given any selected reference point on the same frame, or on a different frame. For example, if a physician finds an abnormality on one frame, he needs to then be able to locate some prominent feature elsewhere in the frame data, i.e., the nipple or a temporary mark placed by the operator, and then find the position of the abnormality relative to that reference point.

Figure 10:
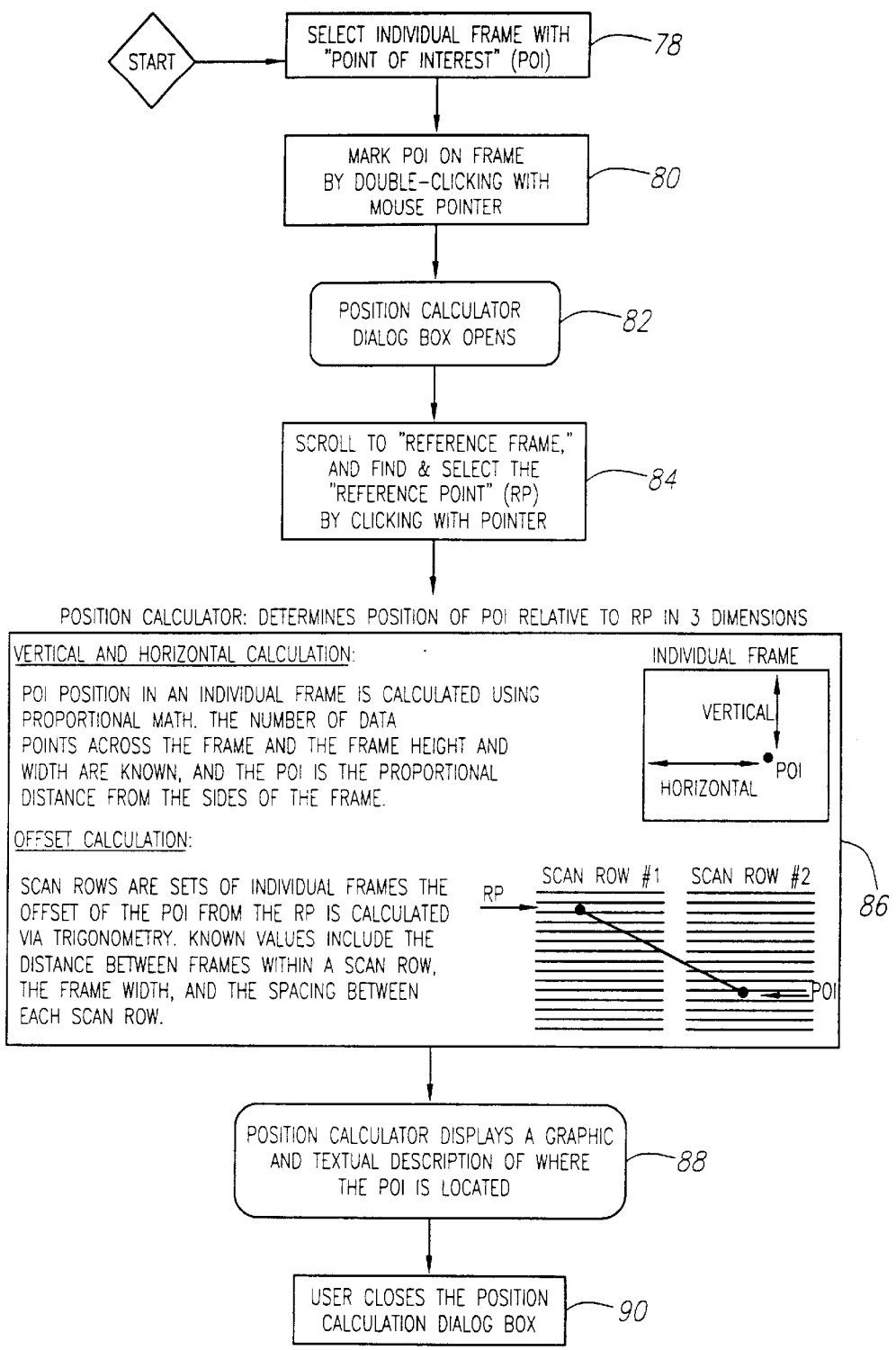
FIG. 10 is a flow chart describing the operation of the viewing program's location function.

The user interface for the location feature operates as shown in the flowchart in FIG. 10. The user marks the point-of-interest ("POI") on a particular frame being viewed 78 by double-clicking it with the computer mouse 80. An overlapped window then appears, and within that window a small display pane shows "thumbnail"-sized sonograph frames taken from the scan rows (actually, the same row "segment") in which the abnormality lies 82. The user can then traverse through the thumb-nailed frames until he locates a reference frame containing a reference point ("RP") he wishes to use 84. In the case of a breast scan, the RP will often be the nipple, which can be positively identified by placing a special pad over the nipple during the scan, readily identifiable on the viewer image. The user can then mark a point on that reference frame using the mouse 84. The viewer program immediately calculates the first position relative to the reference point 86 and displays the results (in both textual and graphical format) to the user 88. The user then closes the dialog box to end the function 90.

To implement the location feature, the viewer takes advantage of the data known about the scan, which is written in the image file's header as part of the data acquisition process. Such information includes the width of the frame, and the distance between subsequent frames in a particular scan row, and the offset between scan rows. Within an individual frame, the location function calculates the position of a user-selected point by proportional math, using the number of image data points (pixels) in the height and width, and the size of the frame, to calculate the distance of the point from the sides of the frame. The program counts the number of pixels across the width of the frame, then the user-selected pixel position number is multiplied by the frame width and divided by the total number of pixels. For example, assuming the frame width is 4 centimeters, the program counts 400 pixels across that width, and the user selected a point at pixel position 100: 100*4 cm/400=1 cm. So the selected point is 1 centimeter from the side of the frame. The program then performs a similar calculation to determine the selected point's distance from the top of the frame. FIG. 10 depicts this process and also shows how the location function determines the distances and angles from a user-selected point of interest (POI) to a user-selected reference point (RP), using the known values and simple trigonometry 86. In breast cancer screening, the POI is usually a suspected cancer, and the RP is the nipple.

The uniform motion of the carrier results in evenly spaced frames, and thus the distance from a reference frame to a particular frame is calculated by counting the number of frames between them and multiplying by the spacing 86. In addition, the overlap of each scan row is known, and thus if the RP is in a different scan row than the POI, determining the location is a simple matter of determining the overlap and measuring the distance, and using trigonometry to make any angular and remaining distance calculations 86. Therefore, counting the frames from the RP and taking into account their overlap provides the location of each individual image.

In a preferred embodiment where the angular position of the probe is dynamically adjusted during the scanning process, the viewing program obtains each frame's angular position during the scan, along with the other information described above. Using that information, the program again uses simple trigonometry to calculate the distances between the RP and the POI.

Another feature of the viewer is its ability to accurately measure the distance between two user-selected points on a single frame. This allows the user to measure anomalies or features found in the images. The process for measuring is very similar to the location function process. Using the known values for frame depth and width, the measuring function uses proportional math to determine the distance between the two points. To measure diagonally across a frame, proportional math is used to determine the lengths of the triangle legs, and simple trigonometry is used to calculate the length of the hypotenuse, which is the distance between the points.

Carrier-less Embodiment

It is possible to obtain the sequential scans without the use of a carrier. The probe is coupled with sensors to provide both location and orientation data that is correlated with each individual frame. The term "coupled" means the sensors could be attached to the probe itself, or used to track the probe's movement without actual attachment. This location and orientation sensor system can provide feedback to the operator to move the probe over the tissue at the correct speed, and to start each scan row in the correct position. This will allow sufficiently complete coverage of the tissue without the need for a mechanized carrier. Alternatively, to obtain relatively uniform spacing of the frames, the speed sensor on the probe can signal the ultrasound scanning device to vary the frame capture rate to match the speed of the probe as it is moved across the tissue.

This carrier-less embodiment does not necessarily rely on the precise movement of the carrier to provide uniform spacing between the frames of a scan row in order to calculate distances between frames. Because location data are available for each frame, the location function of the viewer can use the location information of the POI frame and compare it to the location information of the RP frame, and make the requisite distance and trigonometric calculations to determine the distances from the RP to the POI.

The location and orientation sensor system can be arranged in a variety of implementations. A simple inclinometer can be used to determine the orientation of the probe in two or three axes. The location of the probe can be tracked by an inertial sensor system, or a laser or infrared system, or a radio frequency local positioning system. Alternatively, a simple wheel device could be used to measure distances as well as the speed the probe is being moved over the tissue. Alternatively, an optical movement sensor, such as those commonly used in optical mice, or a laser interferometer, could be attached to the probe to track its movement. When used for scanning breast tissue in conjunction with a covering, the covering could be made of some type of fabric that is compatible with an optical movement sensor. All of these systems could use a point on the body as a reference location, such as the nipple when the system is used for breast scanning.

Method for Tissue Screening

The above-described devices, the probe, scanner, carrier, and viewing program, can be combined to provide a method to scan for anomalies in cellular tissue, such as cancers. The tissue is scanned, and the user views the images on a computer, rapidly scanning through the images in a "movie-like" fashion. This technique causes any anomalies in the tissue to become visible during the rapid sequential playback, as they distort or disrupt normal fibrous planes or sheets. The user can then run the images back and forth until the frame containing the anomaly is found, and the user can mark that anomaly and locate it using the location function of the program. Follow-up studies can be performed using the location information, including a more focused ultrasound investigation, biopsy, etc.

Individual images can be manipulated using image software such as Photoshop, using filters and other manipulation techniques to enhance the appearance of the anomalies and make them more visible. In addition, a variety of image enhancement algorithms are commonly known in the art and the viewer program allows them to be used "on the fly" as the images are displayed in rapid succession.

It is anticipated that the image review process could eventually be automated, once software is developed to identify any anomalies. If necessary, the user could then study the images to determine the accuracy of the software's identification.

Figure 11A:
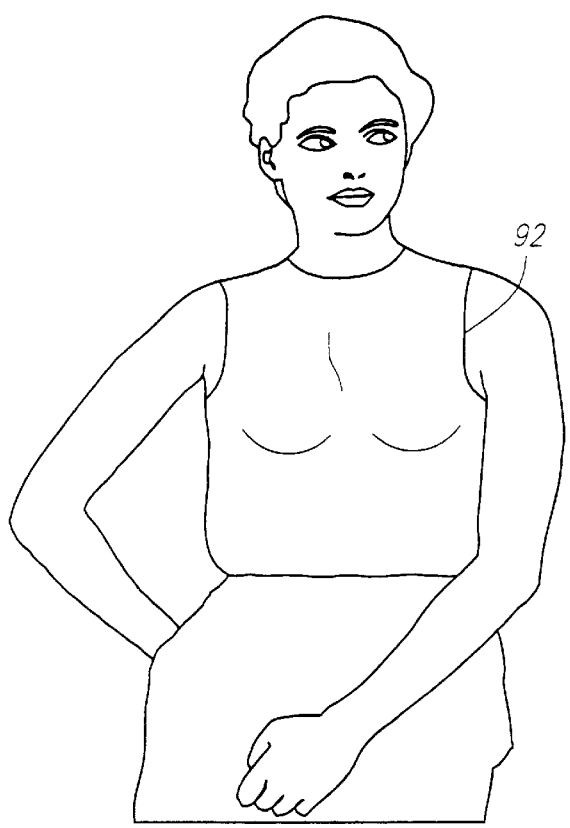
FIG. 11A is a front view of a fabric covering.
Figure 11B:
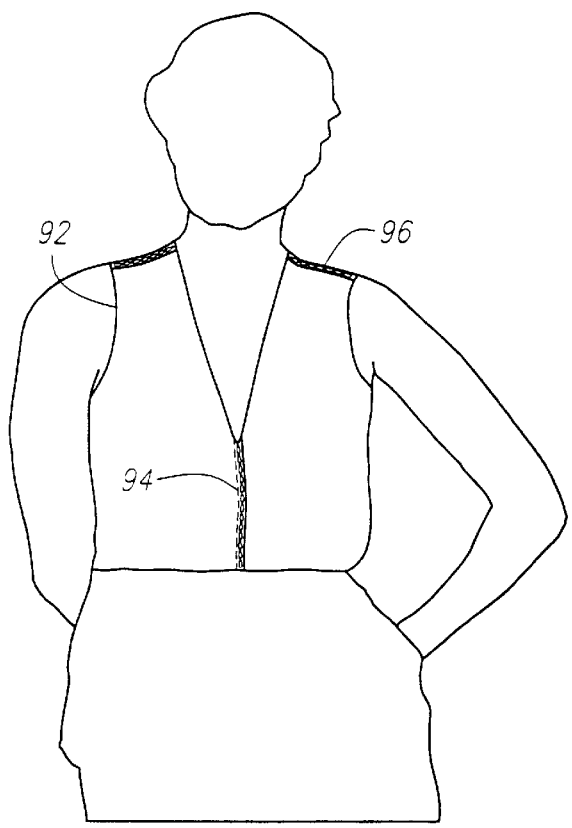
FIG. 11B is a rear view of a fabric covering.

For scanning breast tissue specifically, a preferred methodology is as follows. The mechanical probe carrier is used, and depending upon the size of the probe, the breast may be scanned in strips or in its entirety, in either multiple passes or a single pass, respectively. The breast may be scanned with or without a covering. FIGS. 11A and 11B show a bra-like covering 92 that may aid in holding the breast in position for screening, as well as assisting in uniform integrity of image gathering by reducing information loss from ultrasonic shadowing. The covering also provides some modesty for the patient. Current ultrasound technology requires the use of sonographic coupling agent, usually a gel, to exclude any air between the probe and the skin. Therefore, any such covering would have to be capable of absorbing the gel, and be relatively transparent to ultrasonic energy. The covering could be pre-impregnated with the coupling agent, or the agent could be applied by the operator just prior to the scan, or both. To avoid having the patient pull a gel-soaked covering over her head after the scan is completed, a preferred embodiment of the covering is designed to dismantle after use. The covering is equipped with a seam in the back 94 that is constructed with chain stitching so that the covering may be removed by slipping it off the patient's arms. Chain stitching is similar to that used on bags of dog food and charcoal, where the stitching is easily pulled out just by pulling on one end. The shoulder seams 96 could also be made with chain stitching to further ease removal. Since a preferred embodiment of the covering is designed to be a single-use item, the covering could be cut off with scissors without the need for special stitching. Zippers, hook and loop (velcro™), or other fasteners could also be used to ease the putting on or removal of the covering, and would allow the covering to be re-used. A preferred embodiment uses a stretch fabric for the covering, but any suitable material that can conduct or pass through ultrasonic energy could be used.

Figure 12A:
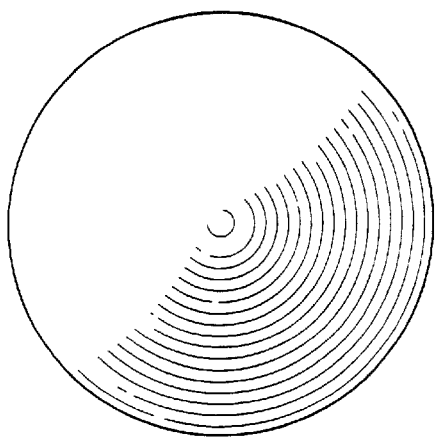
FIG. 12A is a plan view of a nipple pad.
Figure 12B:
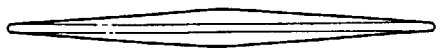
FIG. 12B is a side view of a nipple pad.
Figure 12C:
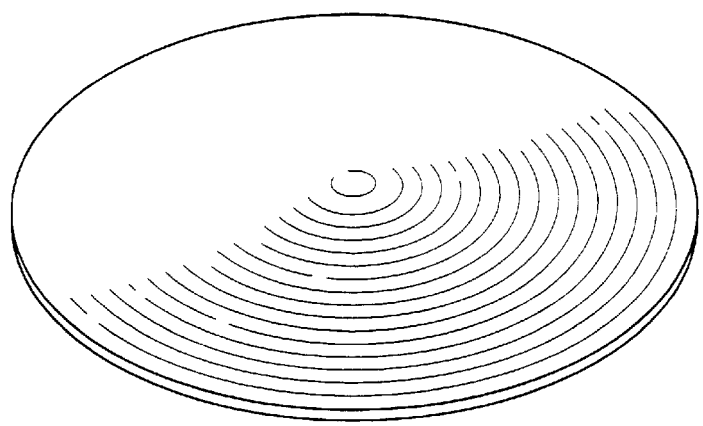
FIG. 12C is a perspective view of a nipple pad.

A nipple pad is placed on each of the patient's nipples to provide a reference point on the images. The nipple pad shows up on the scan images due to its ultrasonic characteristics that distinguish it from the breast tissue. The nipple pad has the added benefit of reducing ultrasonic shadowing. FIGS. 12A, 12B and 12C depict a preferred embodiment of a nipple pad, which is made of an ultrasonically conductive material, such as a solid gel. A preferred embodiment of the pad is approximately 40 mm in diameter and varies in thickness from 1 to 4 mm, but other sizes could be used. Larger and thicker gel pads are commercially available for isolated ultrasound scans, where offsetting the probe from the tissue is advantageous. As shown in FIGS. 12A, 12B and 12C, the circular pad is tapered to an edge about the full periphery of the pad, and has a very smooth surface. The edge of the pad is thick enough to resist tearing, yet thin enough to allow the ultrasound probe to traverse its periphery during scanning without dislodging the pad or causing an ultrasonic shadow at the pad's edge. The pad may be held in place by positioning it beneath the above-mentioned fabric covering.

Another methodology can be used to obtain the images, without the use of a mechanized probe carrier, as described above. Again, the covering and nipple pad may be used.

As described above, the images are reviewed in a rapid sequential fashion, imparting a sense of motion through the breast tissue. The reviewer can observe or detect a disruption of the normal breast architecture through comparative image analysis or observation. The method has advantages over other ultrasound scanning techniques, including the following:

1) Parallel and contiguous images are obtained, optimizing the coverage of the breast tissue and improving the appearance of the images when viewed in a "movie-like" fashion.

2) The entire breast is imaged in a uniform and reproducible manner.

3) The images may be maintained and reviewed singularly, in strip form, or assembled to represent an entire breast, such as 3-D reconstruction.

Accordingly, an improved ultrasonic cellular tissue screening tool is disclosed. Although embodiments and applications of this invention have been shown, it would be apparent to those skilled in the art that many more modifications are possible without departing from the inventive concepts herein. The invention, therefore, is not to be restricted except in the spirit of the appended claims.

What is claimed is:

1. A method of transmitting scan data from a ultrasonic scanning device to a computer, comprising the steps of:

acquiring a desired number of individual scan images as frames within a buffer;

freezing the buffer;

counting the number of frames in the frozen buffer;

determining the dimensions and pixel format for each frame in the frozen buffer;

transmitting the frames from the scanning device to the computer via a connection device;

writing the transmitted frames to an image file in a sequential manner.

2. The method of transmitting scan data from a ultrasonic scanning device to a computer of claim 1, the steps being performed in seriatim.

3. The method of transmitting scan data from a ultrasonic scanning device to a computer of claim 1 further comprising clearing the buffer.

4. The method of transmitting scan data from a ultrasonic scanning device to a computer of claim 1 further comprising opening a file on the computer to accept the frames.

5. The method of transmitting scan data from a ultrasonic scanning device to a computer of claim 1 further comprising converting the frame data from the scanning device format to the format used by a viewer.

6. A method of transmitting scan data from an ultrasonic scanning device to a computer, comprising the steps of performing a handshake sequence between a viewer program implemented by the computer and the scanning device;

clearing an internal memory buffer of the scanning device;

acquiring a desired number of individual scan images as frames within the buffer;

freezing the buffer;

counting the number of frames in the frozen buffer;

determining the dimensions and pixel format for each frame in the frozen buffer;

opening a file on the computer to accept the frames;

transmitting the frames from the scanning device to the computer via a connection device;

converting the frame data from the scanning device format to the format used by the viewer;

writing the converted frame data to an image file in a sequential manner.

7. The method of transmitting scan data from a ultrasonic scanning device to a computer of claim 6, the steps being performed in seriatim.

* * * * *